(12) United States Patent
Ashman (10) Patent No.: US 6,299,763 B1
(45) Date of Patent: Oct. 9, 2001

(54) AUTOGENOUS BONE AND CELL FILTER TRAP

(75) Inventor: Arthur Ashman, 153 Bayberry La., Westport, CT (US) 06880

(73) Assignee: Arthur Ashman, Westport, CT (US)

( * ) Notice: Subject to any disclaimer, the term of this patent is extended or adjusted under 35 U.S.C. 154(b) by 0 days.

(21) Appl. No.: 09/289,308

(22) Filed: Apr. 9, 1999

(51) Int. Cl.[7] ................................................ B01D 35/02
(52) U.S. Cl. ............................ 210/94; 210/448; 210/450; 210/452; 210/455; 210/497.01; 210/499
(58) Field of Search ........................................ 210/446, 448, 210/94, 450, 451, 452, 455, 497.01, 499; 604/319

(56) References Cited

U.S. PATENT DOCUMENTS

| 4,062,781 | * | 12/1977 | Strauss et al. | 210/446 |
| 4,601,820 | * | 7/1986 | Leason | 210/446 |
| 5,100,541 | * | 3/1992 | Kallenbach | 210/448 |

\* cited by examiner

*Primary Examiner*—Matthew O. Savage
(74) *Attorney, Agent, or Firm*—Darby & Darby (57) ABSTRACT

A bone filter trap for harvesting autogenous bone and cell marrow and blood elements collected by an aspirator during medical and dental bone surgical procedures. The bone trap is disposed between the aspirator suction system and the aspirator tip. The bone filter or trap includes housing through which an air flow induced by the suction system is allowed to pass via inlet and outlet openings in the housing. A cylindrically-shaped mesh is longitudinally disposed therein. The cylindrically shaped mesh is open at its top end (facing the inlet opening) and is fitted with a removable solid base at the distal outlet end, such that the induced air flow carrying liquids, solids and gases from the patient surgical site is forced to pass through the mesh. The mesh is sized such that only autogenous bone and cell marrow and blood elements are trapped in the mesh. Upon completion of the medical procedure, the cylindrically-shaped mesh is removed from the inlet and outlet housings. A circularly-shaped plunger device is pushed up and down inside the mesh open end to effectively and efficiently dislodge the elements, (e.g., autogenous bone) trapped inside the cylindrically-shaped mesh and to compress it against the base. The base is removed from the mesh and the compressed autogenous bone mixture is pushed from within the mesh by the action of plunger. The resultant mixture can be utilized alone, or mixed with synthetic or other graft materials (e.g., alloplasts, allografts or xenografts).

19 Claims, 5 Drawing Sheets

FIG. 9f ns # AUTOGENOUS BONE AND CELL FILTER TRAP

BACKGROUND OF THE INVENTION

1. Field of the Invention

The present invention relates to an autogenous bone and cell trap or filter and harvesting system and, more particularly, to a filter capable of collecting autogenous bone and precursor bone cells that are suctioned from a surgical bone site during a surgical procedure and can be harvested for future use, or use during the procedure, to help regenerate bone. This bone "slurry" may be used alone, or in combination with allografts, alloplasts or xenografts.

2. Description of Related Art

Various surgical procedures performed upon a patient result in fluid, solids and other bodily by-products being deposited in the body generally or mouth specifically of the patient. For example, the common ora/maxillofacial procedure for insertion of dental implants often results in the production and deposit of saliva, water, blood, amalgam and other tooth or root fragments and/or autogenous bone in the mouth of the patient. For health and sanitary reasons, it is generally desirous to continually remove these by-products through suction throughout the procedure in order to the improve the observation of the surgical site by the surgeon and to avoid infection which can occur if these objects are permitted to remain in the area adjacent to the surgical site or body of the patient.

Accordingly, aspirators are commonly employed to continuously remove by-products produced during oral/maxillofacial and general surgical and non-surgical procedures. An aspirator is typically embodied as a narrow-tipped, hand held tube connected to a flexible hose. The hose is attached to an electric motor driven suction system which draws air through the hose forming a vacuum, such that the tip of the hand-held tube continuously removes the undesirable solid, liquid and gaseous by-products resident at the surgical or other procedure site in the patient's mouth or body.

Though many of the products removed from the patient's body during these procedures are infectious and generally undesirable, osseous materials, such as autogenous bone, are an exception. Autogenous bone carries gross bone particles, stem cells and other blood elements necessary for regeneration of new bone. Accordingly, the separation and collection of the autogenous bone (also known as "bone harvesting") resulting from surgical, medical and dental procedures is a desirable goal.

The types of bone harvesting devices presently available utilize an existing aspirator system in conjunction with a filtering device to capture autogenous bone traveling in the air flow induced by the suction system. One such filter comprises a solid, non-transparent body which connects directly to the aspirator tip and traps osseus bone in an enclosed mesh basket. The autogenous bone is thereafter collected by scraping the basket to dislodge the autogenous bone. Because of the basket shape of the mesh, it is difficult to remove all of the autogenous bone captured in the mesh. Also, because the body of the filter is non-transparent, it is impossible to know when the mesh basket has reached its capacity in instances where a large amount of autogenous bone is collected. Other bone harvesting devices utilize generally flat, peel-back mesh filter elements. (See U.S. Pat. No. 5,766,134 issued to Arab) Such devices can be used only once and are difficult to sterilize, subject to clogging and contamination with bad elements that would normally pass through the filter and are therefore costly to utilize.

SUMMARY OF THE INVENTION

Accordingly the present invention is directed to providing a transparent and disposable apparatus, as well as a method for efficiently trapping and collecting autogenous bone removed from a patient by an aspirator system during medical or dental procedures in which autogenous bone along with its marrow elements may be dislodged.

In an illustrative embodiment of the present invention, an autogenous bone trap or filter has a substantially cylindrical housing or body portion with narrower hollow cylindrical projections extending longitudinally from each end thereof. These projections allow the standard hollow flexible tubing used in aspirator systems to be connected to each end of the cylindrical housing body. The tubing at a proximal or inlet end of the cylindrical body extends to a conventional aspirator tip and the tubing at the distal or outlet end extends to the aspirator suction motor. As a result, the bone trap may be placed anywhere between the tip and the aspirator suction motor.

A cylindrically-shape mesh of lesser diameter than the cylindrical body or housing has a removable solid base mounted at its proximal end and an open circular area at its distal end. The base is in the form of a tray with a peripheral ring and a raised disk-shaped surface mounted on the ring by a connecting circular wall. The cylindrical body of the trap is made as two sections which can be separated so the mesh and base can be placed within the main body portion of the suction trap so that the open end of the mesh faces the inlet of the bone trap. Accordingly, when flow is induced by the suction system, the liquids, solids and gases which are captured by the aspirator tip are forced to pass along the tubing from the tip to the inlet projection of the cylindrical body, into the open end of the cylindrical mesh, laterally through the mesh to the cylindrical body wall, along the wall to the outlet projection and through further tubing to the suction motor. The mesh is appropriately sized such that autogenous bone particles and cells that are too large to pass through the mesh are collected on its inner wall and on the surface of the tray that blocks the end of the mesh.

Because the body of the bone trap is transparent, the amount of autogenous bone collected by the mesh may be visually monitored by the user of the present invention. This prevents clogging and contamination on by elements that would normally pass through.

When the procedure is completed, the two housing sections of the cylindrical body are manually separated. Before and after the cylindrical mesh and tray are removed, a circularly-shaped plunger device is then utilized to scrape the inner walls of the cylindrical mesh. The plunger is moved into the open end of the mesh and toward the tray, such that substantially all of the autogenous bone and marrow elements are removed from the mesh inner wall and pressed onto the tray. The tray is removed manually and the compressed autogenous bone is left on the surface of the sample tray, where it can be conveniently and effectively removed and used either alone, or in combination with other materials (e.g. alloplasts, allogafts or xenografts).

BRIEF DESCRIPTION OF THE DRAWINGS

Various features of the present invention will be described hereinafter in detail by way of preferred embodiments with reference to the accompanying drawings, in which.

DESCRIPTION OF THE PREFERRED EMBODIMENTS

Figures 1, 2A:
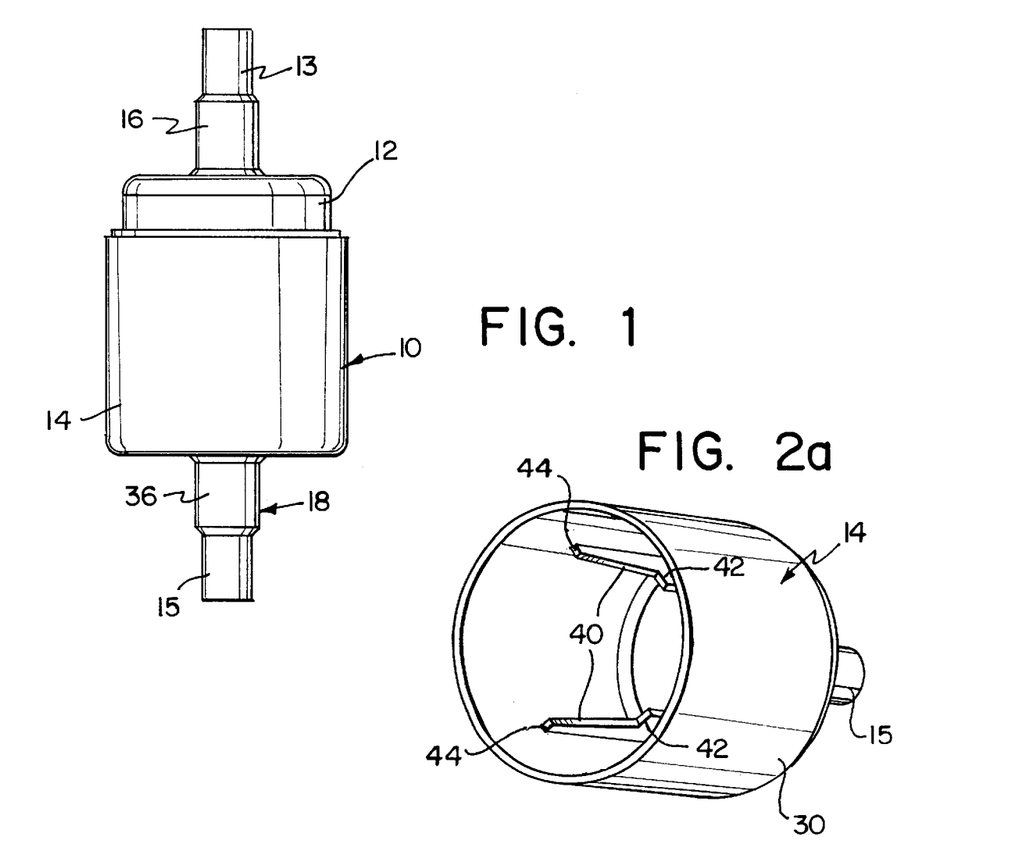
FIG. 1 is a side perspective view of a bone filter or trap of the present invention.
FIG. 2(a) is a perspective view of the outlet section of the cylindrical housing of a bone trap of the present invention.
Figure 7:
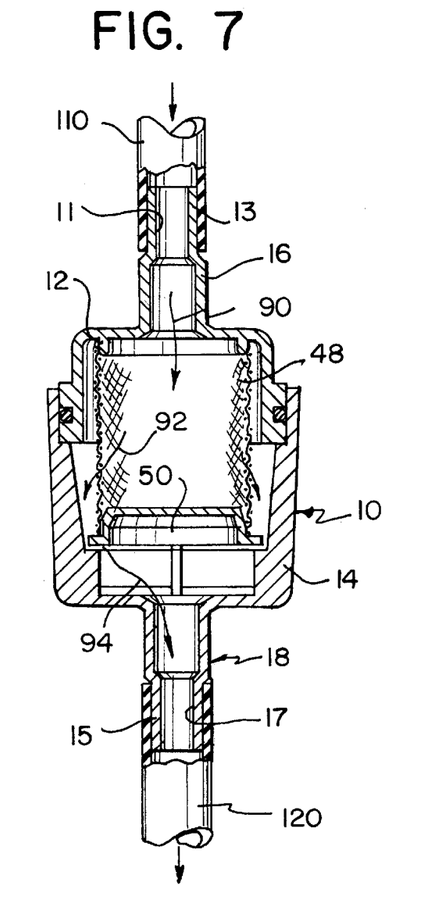
FIG. 7 is a representation of the flow path through the bone trap of FIG. 6.

The filtration and collection of autogenous bone is accomplished by means of a filter device placed between a handheld aspirator tip and the suction systems of the aspirator. FIG. 1 illustrates such a suction filter trap for filtering autogenous bone fragments from the fluid suctioned by an aspirator during oral/maxillofacial or other surgical or medical procedures. The filter trap may also filter cellular elements, e.g., bone precusor cells, in the fluid and gross specules of autogenous marrow bone elements. The device includes a hollow body or housing 10 of substantially cylindrical shape. The body 10 is separated into an inlet housing section 12 and an outlet housing section 14. Extending from the inlet section 12 is a narrower cylindrical projection 16, and a narrow cylindrical projection 18 extends from the outlet housing section 14. As shown in FIGS. 1 and 7, a fitting 13 on the projection 16 forms an inlet opening 11 for the trap and is adapted to receive a flexible hollow tube 110 connected to a hand-held tip (not sown) of an aspirator device. A fitting 15 of the projection 18 forms an outlet opening 17 for e filter trap and is adapted to receive a flexible hollow tube 120 connected to the vacuum motor (not shown) of an aspirator device.

A cylindrically-shaped mesh screen 48 is mounted within the hollow body 10 to intersect the flow path of the suction system such that autogenous bone particles being carried by the flow are caused to be trapped within the cylindrically shaped mesh screen 48 for later collection and use.

Figure 2B:
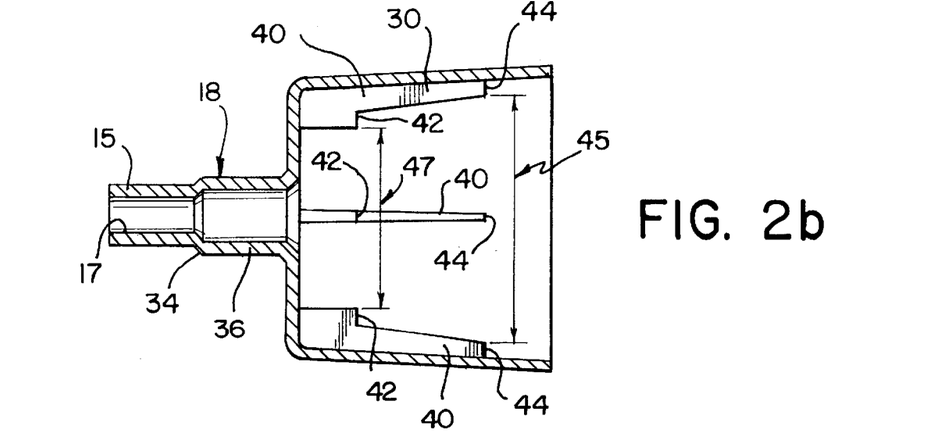
FIG. 2(b) is a cross-sectional view of the outlet section of the cylindrical housing of FIG. 2(a)
Figure 2C:
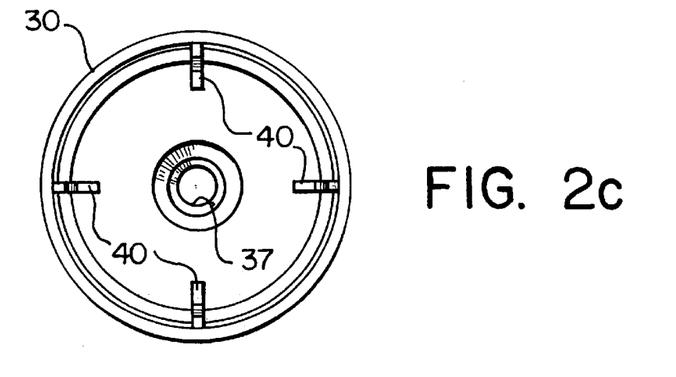
FIG. 2(c) is a left side elevation of the cylindrical housing of FIG. 2(a).

FIGS. 2(a)–2(c) illustrate various views of the outlet section 14 of the housing of the bone filter device. The outlet section housing 14 comprises a substantially hollow cylindrical main body portion 30 with the narrower cylindrical projection 18 extending longitudinally therefrom. The diameter of the outer surface of the cylindrical main body portion 30 is substantially constant throughout its length. In the preferred embodiment, the outer surface of the main body portion 30 has a diameter of approximately 1.625".

The diameter of the projection 18 is two-tiered, the diameter of that portion connected to the main body part 36 being greater than the second part 15, and both being significantly smaller than the diameter of the main body portion 30. The sharp taping of the longitudinally extending portion 18 between portions 36 and 15 forms an edge or lip 34 against which the hollow tubing terminus can be securely attached. In the preferred embodiment, the diameter of the first portion 36 of the longitudinally extending projection 18 is approximately 0.435", and the width of the second portion 15 measures approximately 0.34". The overall length of the projection 18 is about 0.965".

Because gases such as air molecules seek to maintain a constant pressure, a reduction in volumetric space (from the main body portion 30 to the longitudinally extending portion 18) will cause the speed of the traveling air molecules to increase beyond the mesh so as to maintain a constant flow rate. Therefore, the reduction in volumetric space between the main body portion 30 and the projection 18 increases the suction effect of the air flow through the body portion. In the preferred embodiment, the diameter of the inner surface of the main body portion measures proximately 1.618" and the diameter of the second part 38 of the projection 18 measures approximately 0.2".

Also, the extension of the flow cross section as the flow enters the inlet housing causes the flow rate to drop, thus permitting better filter action. The enlarged filter also allows for increased surface area for the mesh, which also improves filtration The inner walls of the main body porion 30 support four lateral support projections 40. The support projections 40 form a slight edge or seats 44, then angle sharply inward along the longitudinal direction until the support projections 40 again become substantially flat, forming a second set of seats 42 upon which a circular object can be supported laterally with respect to the wall of the inner surface of the main body portion 30. In the preferred embodiment, the distance between the proximate ends of facing seats 44 measures approximately 1.350" (See line 45 in FIG. 2(b)). The distance between the proximate ends of the facing seats 42 measures approximately 1.0". (See line 47 in FIG. 2(b)).

In the preferred embodiment, the outlet housing, as well as all other components of the bone trap (except for the mesh and the gasket described below) are preferably manufactured by injection molding high-impact polypropylene. It is recognized, however, that other sterilizable plastics, e.g., transparent plastics, and/or manufacturing techniques could be used. The preferred embodiment requires only that the bone trap be capable of withstanding the pressure induced by the air and fluid flow through the bone trap device produced by standard medical aspiration systems.

Figure 3A:
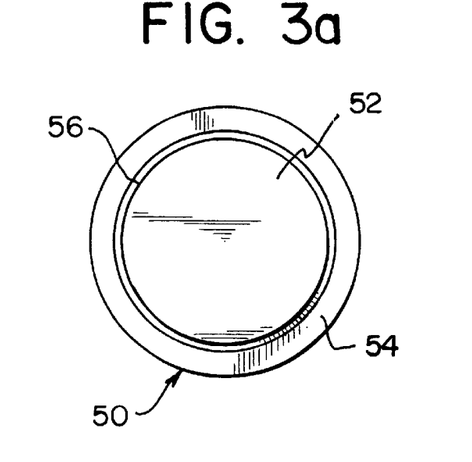
FIGS. 3(a) and 3(b) are top plan and side views of the collection tray of a bone trap of the present invention.
Figure 3B:
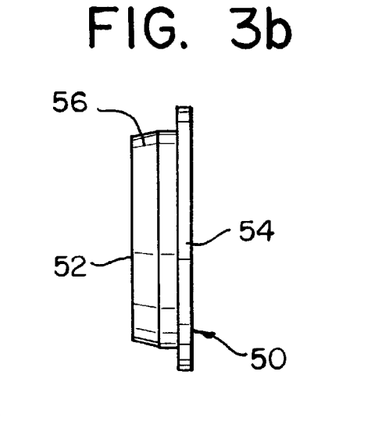

Two views of a circular surface of an inverted tray 50, which is used as a base for the mesh filter in the assembled device, are shown in FIG. 3(a) and 3(b). This tray can be seated upon the second set of seats 42. The tray 50 has a raised a platform 52 and a ring or lip 54 formed around the outer edge of the tray and connected to the platform 52 by an annular side wall. The side or connecting wall 56, which forms the transition from platform surface 52 to lip 54, is slightly tapered and is of a height that allows secure retention of the tubular filter mesh 48 on to the tray. In the preferred embodiment, the platform 52 has a diameter of approximately 0.876" and the overall height of the sample tray from the bottom portion of the lip 54 to the upper portion of the platform 52 measures approximately 0.250".

Figure 4:
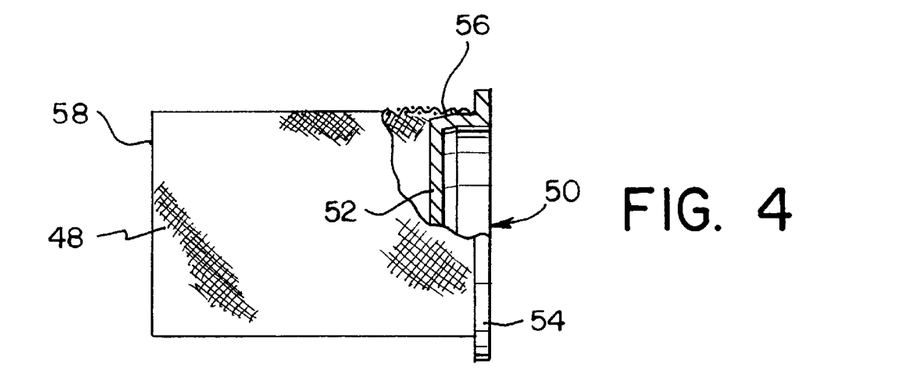
FIG. 4 is a side view with parts broken away of the cylindrical mesh of the present invention mounted on the sample tray of FIGS. 3(a) and 3(b)

The filter mesh 48 and sample tray 50 are illustrated in FIG. 4. In the preferred embodiment, an 80 micron mesh measuring 160×155 mms is formed into a cylindrical shape with a height measuring approximately 1.25" and a diameter of approximately 0.950" (slightly greater than the diameter of the raised platform of the tray) such that the mesh 48 can be securely positioned on the tray 50 as shown in FIG. 4. Other dimensions and mesh sizes may also be used effectively.

The cylindrical mesh remains open at the distal end 58 of the cylinder opposite the tray 50 such that the mesh 48 and tray 50 form a cylinder closed at one end and opened at the other so that fluid flow enters unimpeded at the mesh's open end 58 and is forced to exit laterally through the openings in the mesh 48 because of the tray 50. The dimensions of the openings of the mesh 48 preferably, (80 microns) are such that autogenous bone is retained by the mesh 48 while other nonresinous elements and fluids are allowed to pass through the mesh 48 and out of the main body potion 30.

Figure 5A:
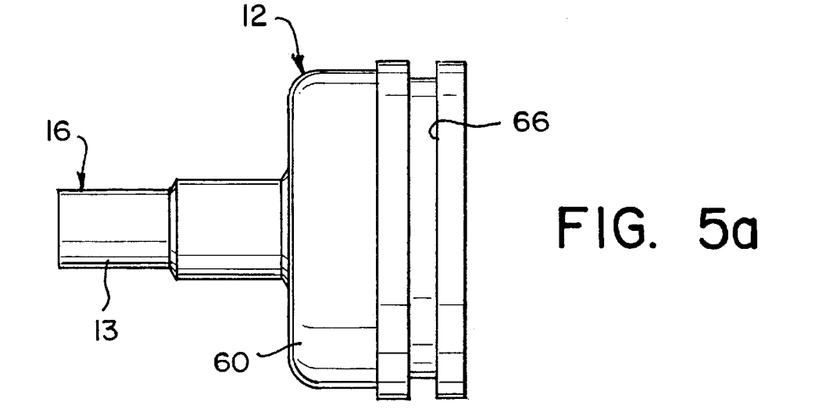
FIG. 5(a) is a side view of the inlet section of the cylindrical housing of a bone tap of the present invention.
Figures 5B, 5C:
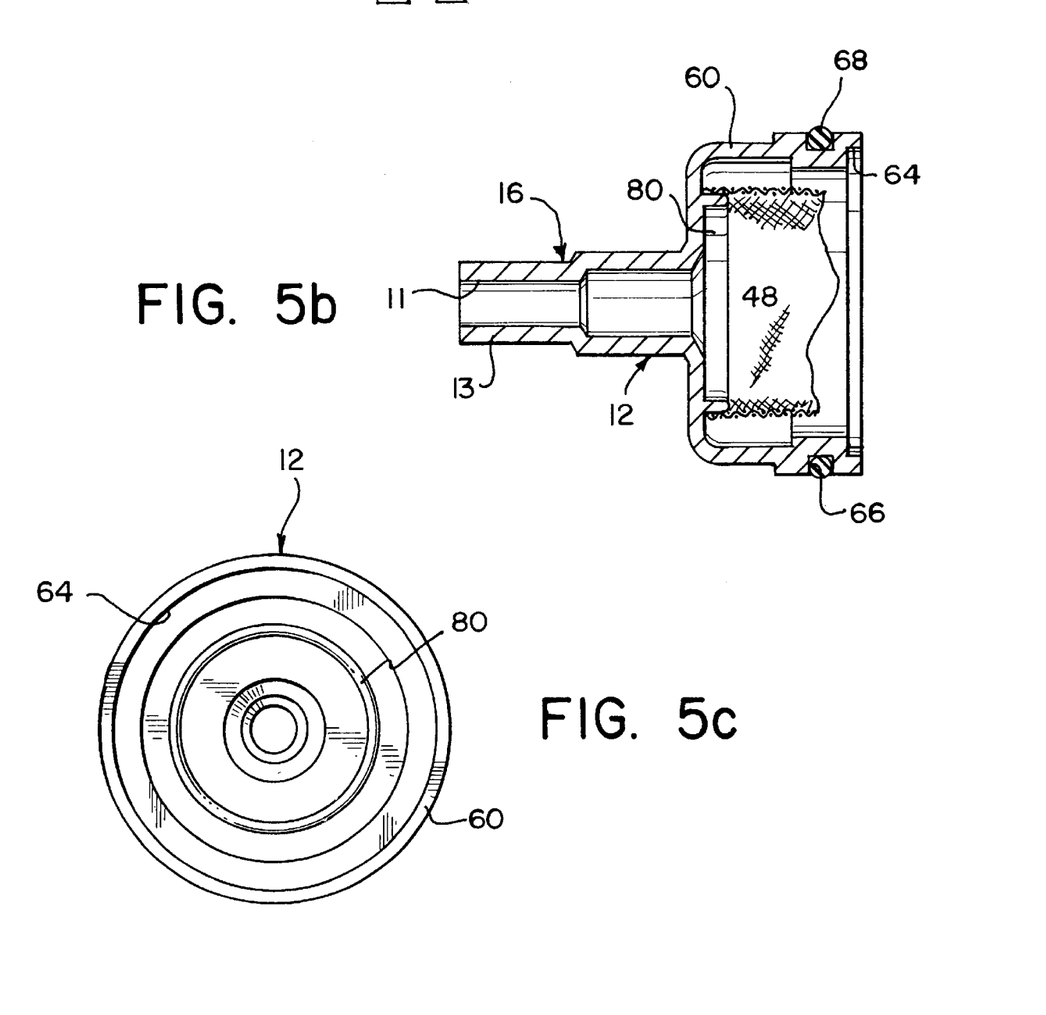
FIG. 5(b) is a cross-sectional view of the inlet section of the housing.
FIG. 5(c) is a right side view of the inlet section of the housing.

FIGS. 5(*a*)–(*c*) illustrates various views of the inlet housing 12 of the bone trap 10. The inlet housing comprises a substantially hollow cylindrical main body portion 60 with a narrower cylindrical projection 16 extending longitudinally from the main body portion 60. The outer diameter of the main body portion 60 is dimensioned such that the large opening portion 64 of the inlet housing can be frictionally secured in the large open portion of the outlet housing 30. To insure further sealing, a groove 66 is present around the circumference of the main body portion 60 into which a annular seal ring or gasket 68, preferably made from elastomeric material, is deposited. When the large opening 64 of the inlet housing is fitted into the large opening of the outlet housing 30, the gasket 68 forms a fluid and vacuum-tight seal between the two housings. In the preferred embodiment, the diameter of the main body portion 60 of the inlet housing measures approximately 1.617" and the width of the groove 64 into which the seal ring is secured measures approximately 0.1100".

The cylindrical width of the outer portion of the projection 16 is two-tiered in a manner similar to the projection 18 of the outlet housing for the similar purpose of providing a seat for flexible hollow tubing to be securely fitted to the inlet of the bone trap.

The cylindrical width and height of the inner portion of the inlet housings main body 60 is formed such that the open end 58 of the filter mesh 48 will fit securely in the inlet housing when the inlet housing and outlet housing are brought together and sealed by the frictional force of the gasket 68. Furthermore, a ring 80 is formed on the distal wall of the inlet housing. The ring 80 is sized such that the open end 58 of the mesh 48 fits against it and is held in place. In the preferred embodiment the ring 80 has a diameter of approximately 0.949" (i.e., slightly less than the diameter of the mesh) and protrudes longitudinally into the housing by approximately 0.1".

The measurements described herein are merely exemplary and are not intended to limit the scope of the invention. Such measurements may vary to a wide degree depending on manufacturing techniques and fit acceptable for a particular type of aspirator equipment. The bone trap of the of the present invention can thus be constructed to fit a variety of aspirators and tips in many combinations.

Of course, the overall shape of the bone trap of the present invention may vary depending on these measurements. Furthermore, junctures between ledges and walls of the bone trap may be rounded to a variety of radii and wall thicknesses, and edge projections may vary in a large range.

Figure 6:
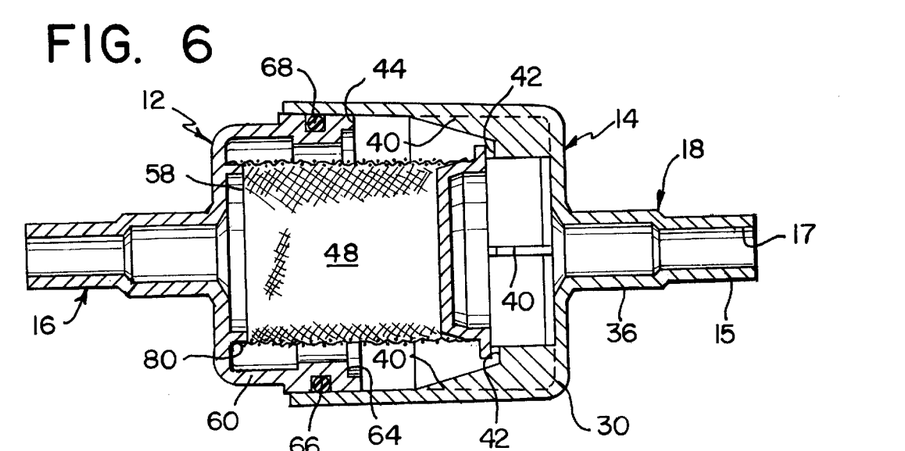
FIG. 6 is a cross-sectional view of an assembled bone trap according to the present invention.

The method of assembling the various parts to form a bone trap will now be described with reference to FIG. 6.

The mesh 48 and the tray 50 are assembled and are placed into the main body portion 30 of the outlet housing forming a filter element. The filter element is disposed such that the tray 50 of the filter element rests upon the seats 42 formed by the lateral flanges 40. In this way, the opening of the mesh 58 is in the same plane as the large opening of the outlet housing.

The large opening of the inlet housing is then brought into frictional contact with the inner walls of the outlet housing at the large opening end of the outlet housing. Manual pressure is applied to both the inlet and outlet housings until the edge of the inlet housing makes contact with the four seats 44 formed by the lateral flanges 40 of the outlet housing. The seats 44 are positioned with reference to the outlet housings inner wall such that when contact is made with the inlet housing, the gasket 68 will have formed an annular seal between the inner wall of the outlet housing and the outer wall of the inlet housing. Effectively, the two housings will be sealed, such that the only flow path for air, fluid or debris from outside the bone trap will be through the openings in the longitudinal projections 16 and 13 of the outlet and inlet housings, respectively.

The seats 44 of the lateral flanges 40 of the outlet housing are positioned with the further purpose of tightly securing the mesh filter in the bone trap. As is shown in FIG. 6, the height of the mesh is appropriately sized such that, when the inlet and outlet housings meet at the seats 44, the open side of the mesh is engaged and held firmly in place by the ring 80 formed on the distal side wall of the inlet housing. The ring 80 insures the structural integrity of the mesh by supporting the cylindrical structure when high pressure flow is induced through the attached suction system.

FIG. 7 illustrates the flow path of air, solids and liquids through the bone tap. The cylindrical projection 16 of the inlet housing is connected to standard flexible hollow tubing 110, the distal end of which is connected to a handheld hollow aspirator tip placed in the mouth or body of the patient. The cylindrical projection 18 of the outlet housing is likewise connected to standard flexible tubing 120. The other end of the tubing 120 is connected to the suction system of the aspirator. Upon activation of the suction system, air flow is induced from the tip of the hand-held device through the bone trap and into the suction system. The airflow creates a vacuum in the mouth or body of the patient, such that all unencumbered liquids, solids and gases in the patient's mouth or body within a certain proximity to the tip are drawn into the tip device, through the flexible tubing and into the bone trap. The flow of liquid, solids, and gases then proceeds into the open end of the mesh 48 (arrow 90). The tray 54 of the mesh filter is solid, the air flow must proceed laterally through the lattice of the mesh as shown by arrow 92. The size of the lattice in the mesh allow all liquid, fine solids and gasses being carried by the air flow to pass, except for significantly sized autogenous bone and other cellular marrow elements Hence, the autogenous bone and stem cells are collected or harvested by the interaction between the mesh and the airflow, and is left deposited on the inside of the mesh. The airflow carrying the remaining liquid, gases and solids removed from the patient's mouth or body proceeds through the cylindrical projection 18 of the outlet housing and through the flexible tubing 120 to the aspirator suction motor.

Figure 8A:
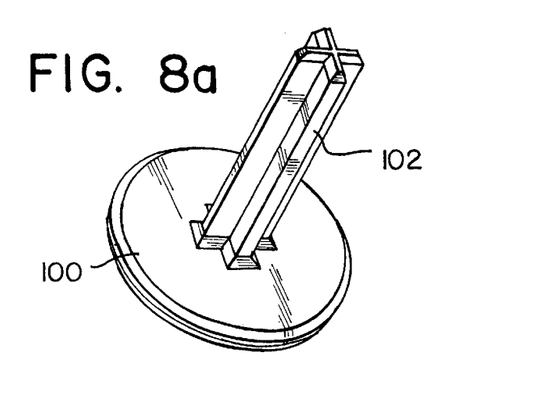
FIG. 8(a) is a rear perspective view of a plunger for use in removing autogenous bone fragments from a cylindrical mesh of the present invention.
Figure 8B:
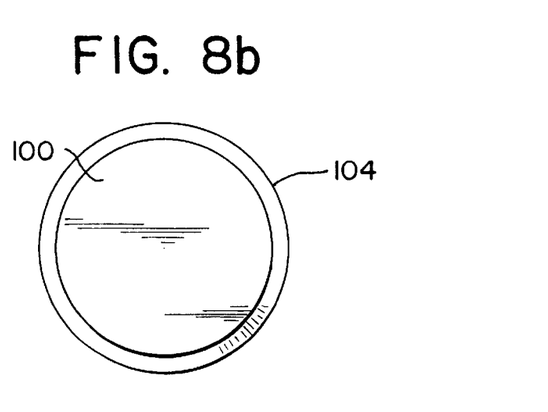
FIG. 8(b) is a front plan view of the plunger of FIG. 8(a)
Figure 9A:
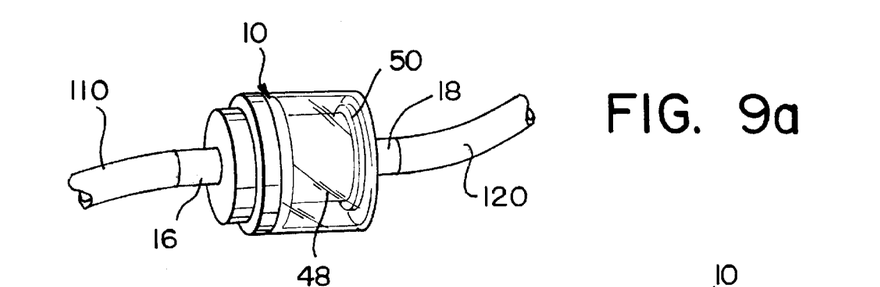
FIGS. 9(a)–9(f) illustrate the method of using the plunger of FIG. 8(a) to remove autogenous bone from the cylindrical mesh.
Figure 9B:
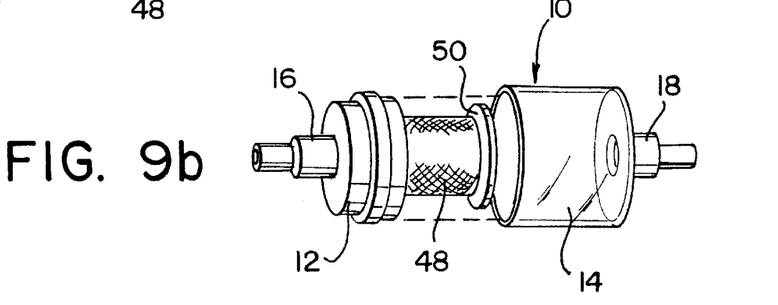
Figure 9C:
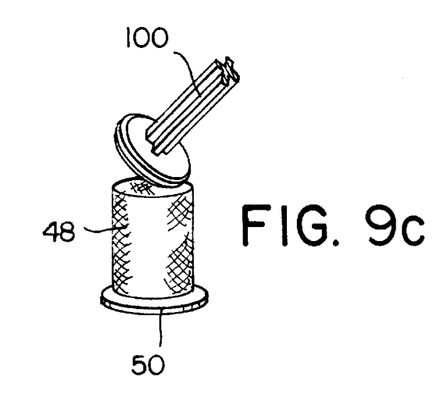
Figure 9D:
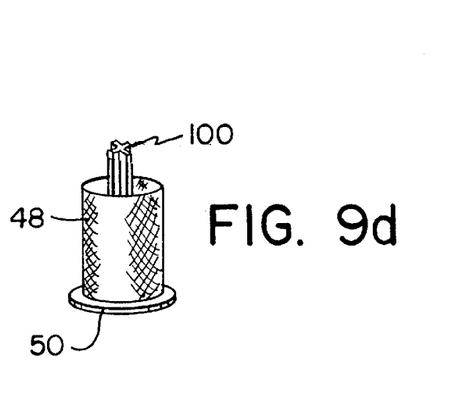
Figure 9E:
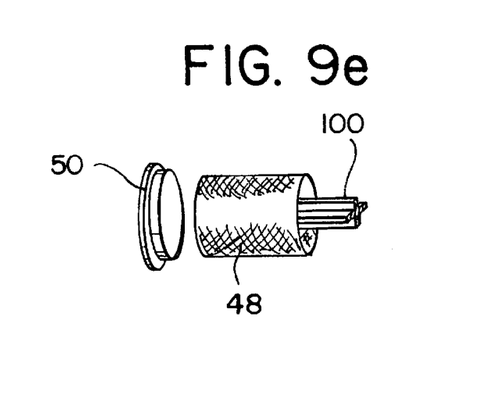
Figure 9F:
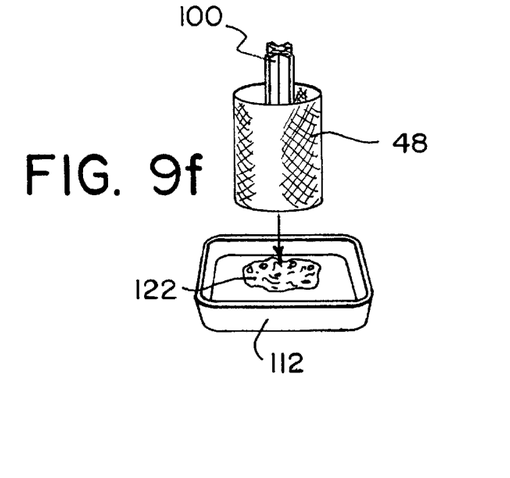

The autogenous bone and other cellular marrow element are removed from the mesh filter through the use of a plunger illustrated in FIGS. 8*a* and 8*b*. The plunger 100 is comprised of a circular base 104 and an elongated stem 102 attached to the center of the circular base 104. Although in the preferred embodiment the stem 102 has a cross-shaped cross-section, it may, of course, have any suitable shape, e.g., round. The diameter of the circular base 104 is sized to conform to the inner dimensions of the cylindrical mesh 48, such that when the circular base 100 is inserted into the open end of the mesh 48, the edges of the circular base 104 come into contact with the inner surface of the mesh 48, causing the autogenous bone to be disengaged from the mesh 48. In the preferred embodiment, the circular base 104 is formed to have a diameter of approximately 0.935". The plunger stem 102 is sized to have a length greater than the height of the mesh netting (approximately 1.25").

FIG. 9 illustrates the method of harvesting the autogenous bone. FIG. 9(*a*) shows the bone trap immediately following an oral/maxillofacial or some other surgical procedure wherein autogenous bone and cellular elements are deposited inside the mesh 48. Because in the preferred embodiment, the housing 10 is transparent, the amount captured in the trap can be viewed. The flexible tubing is then removed from the inlet 16 and outlet 18 of the bone trap and, as shown in FIG. 9(*b*), the inlet housing is manually separated from the outlet housing by applying a minimal amount of pressure to overcome the friction holding the two housings together. Note that the inner housing ring 80 anchors the mesh filter 48 to the inlet housing. As shown in FIG. 9(*c*) and (*d*), the mesh filter is removed from the inlet housing and the circular base end of the plunger is inserted into the open end of the mesh cup and downward pressure is applied. This action causes the sides of the circular base 104 to dislodge the autogenous bone and cells deposited on the inner walls of the circular mesh 48 and to press it towards the surface 52 of the tray 50. The downward pressure compacts the autogenous bone toward the tray 50 of the mesh filter. This can be repeated by moving the plunger up and down inside the mesh to ensure that most of the bone and cell elements have been dislodged.

Once the user is satisfied that most of the autogenous bone and the other cellular elements have been dislodged from the mesh, the tray 50 is manually removed from the mesh as shown in FIG. 9(*e*). Finally, the mesh 48 is held over a sterile so dish 112 or some other suitable container. As shown in FIG. 9(*f*) the plunger is fully inserted through the distal end of the mesh causing the compacted mass 122 to fall onto the specimen dish 112.

The collection of compacted autogenous bone can then be used, for example, alone or in combination with synthetic bone grafts, e.g., Bioplant®, HTR®, (alloplasts) or allografts or xenografts to fill alloplasts an extraction socket, or any bony void around dental or medical implants, in any oral/maxilla facial or medical bony surgical procedure.

While the present invention has been particularly shown and described with reference to preferred embodiment thereof, it will be understood by those skilled in the art that various changes in form and details may be made therein without departing from the spirit and scope of the invention.

What is claimed is:

1. A filter trap for collecting autogenous bone and other cell marrow and blood elements suctioned from a surgical site, comprising:

a hollow housing having an inlet and an outlet adapted to be connected in line in the tubing of an aspirator;

a generally tubular-shaped filter mesh extending between said inlet and outlet of said housing, one end of said tubular-shaped filter mesh being open to the inlet of said housing so that all of the flow entering said housing enters the interior of said tubular-shaped filter mesh;

a substantially planar non-porous sample surface removably disposed and extending completely across the other end of said tubular-shaped filter mesh so as to block flow therethrough and to force flow through a side wall of said tubular-shaped filter mesh; and support projections within said housing to support said filter mesh and sample surface in a position spaced apart from an interior surface of said housing, and to permit flow that has passed through the filter mesh to travel along the interior surface of said housing to the outlet thereof.

2. The filter of claim 1 wherein said housing is formed from an inlet housing section and an outlet housing section, said housing sections being separable, each housing section having a cylindrical shape with a diameter of one being larger than the other so that one fits at least partially within the other to form the housing, said inlet housing section having a tubular projection to form said inlet and said outlet housing section having a tubular projection to form said outlet.

3. The filter of claim 2 wherein said tubular projections form seats for tubing of an aspirator.

4. The filter of claim 2 wherein said inlet housing fits within said outlet housing and said support projections extend from an interior surface of said outlet housing and forms a seat for said sample surface, and further including a ring projecting from a distal wall of said inlet housing which engages the open end of the tubular-shaped filter mesh.

5. The filter of claim 2, wherein said diametrically larger housing section further includes a seating surface extending radially inward from an inner surface thereof and adapted to engage said other housing section.

6. The filter of claim 2, wherein said outlet housing further includes a seating surface extending radially inward from an inner surface thereof and adapted to engage said inlet housing.

7. The filter of claim 1, wherein said support projections are formed of plastic.

8. A filter trap for collecting autogenous bone and cell marrow and blood elements suctioned from a surgical site comprising:

a hollow outlet housing having an inlet opening and an outlet projection generally axially aligned, at least two support projections extending generally radially inward from an inner surface of said outlet housing, said support projections forming seating surfaces, said seating surfaces being generally radially inwardly disposed from said inner surface of said outlet housing;

a hollow inlet housing having an inlet projection and an outlet opening, said outlet opening of said inlet housing being selectively engageable with said inlet opening of said outlet housing;

a sample tray having a substantially planar first surface and a second surface, said second surface being axially disposed from said first surface toward said outlet projection and radially disposed from said first surface and having a shape generally adapted to seat on said seating surfaces of said outlet housing; and a generally tubular-shaped filter having an inlet end, an outlet end, and a filter mesh extending between said inlet and outlet ends, said outlet end having a shape generally adapted to seat against said second surface of said sample tray so that said first surface is removably disposed and extends completely across said outlet end, said inlet end having a shape generally adapted to seat against a ring projecting from a radial distal wall of said inlet housing about its inlet.

9. The filter of claim 8, wherein said inlet housing is slidingly engageable with said outlet housing.

10. The filter of claim 8 further including a gasket between said outlet opening of said inlet opening housing, and said inlet opening of said outlet housing.

11. The filter trap of claim 10, wherein said gasket is formed from an elastomeric material.

12. The filter of claim 8 wherein dimensions of openings of said mesh are approximately 80 micron.

13. The filter of claim 8 wherein said inlet opening of said inlet housing has a lip extending generally axially from said inner surface of said inlet housing toward said outlet of said inlet housing, said lip having a shape generally conforming to the inner surface of said inlet opening of said filter.

14. The filter of claim 8 wherein said inlet opening of said inlet housing is adapted to receive an aspirator hose.

15. The filter of claim 8 wherein said outlet of said outlet housing is adapted to receive an aspirator hose.

16. The filter trap of claim 15 wherein said housings and said sample tray are formed from sterilizable plastic.

17. The filter of claim 8 wherein said outlet housing has four of said support projections.

18. The filter of claim 8 wherein said housings are formed from a transparent material.

19. The filter of claim 8, wherein said seat seating surfaces are formed of plastic.

* * * * *